United States Patent [19]

Schroth et al.

[11] Patent Number: 5,385,934
[45] Date of Patent: Jan. 31, 1995

[54] METHODS FOR PREVENTING PRECIPITATION OF COPPER FROM COPPER BASED BACTERICIDAL COMPOSITIONS CONTAINING IRON

[75] Inventors: Milton N. Schroth, Orinda; Yung-Ann Lee, Albany; Mavis D. Chong, El Sobrante, all of Calif.

[73] Assignee: The Regents of the University of California, Oakland, Calif.

[21] Appl. No.: 46,581

[22] Filed: Apr. 12, 1993

Related U.S. Application Data

[63] Continuation-in-part of Ser. No. 644,997, Jan. 22, 1991, Pat. No. 5,202,353.

[51] Int. Cl.⁶ .............................................. A01N 55/02
[52] U.S. Cl. ...................................... 514/500; 514/502
[58] Field of Search ................. 504/152; 514/500, 502

[56] References Cited

U.S. PATENT DOCUMENTS

| | | | |
|---|---|---|---|
| 2,924,551 | 2/1960 | Harwood et al. | 167/22 |
| 4,101,669 | 7/1978 | Baude et al. | 424/286 |
| 4,193,993 | 3/1980 | Hilditch | 424/141 |
| 4,286,988 | 9/1981 | Castelli et al. | 106/15.05 |
| 4,297,436 | 10/1981 | Kubotera et al. | 430/310 |
| 4,670,429 | 6/1987 | Dombay et al. | 514/187 |
| 4,745,129 | 5/1988 | Ikari et al. | 514/502 |

OTHER PUBLICATIONS

Clarke et al., Applied and Envir. Microbio., May 1987, pp. 917–922.
Journal D'Agriculture Pratique, pp. 698–700, 728–729 and 965–766 (1887).
Lodeman, "The Spraying of Plants", pp. 19–50, The MacMillan Company, New York, New York (1910).
Millardet, "Note Sur Les Vignes Americaines et Opuscules Divers Sur le Meme Sujet", pp. 56–60 (1881).
Millardet, "The Discovery of the Bordeaux Mixture" (1885) Translated (from French) by Schneiderhan, pp. 13–15 (1933).

*Primary Examiner*—Richard L. Raymond
*Assistant Examiner*—Brian M. Burn
*Attorney, Agent, or Firm*—Burns, Doane, Swecker & Mathis

[57] ABSTRACT

Disclosed herein are copper based fungicidal and bactericidal compositions having enhanced activity against fungi and bacteria, methods of using such compositions as well as methods for increasing the effectiveness of the copper based fungicidal and/or bactericidal compounds employed in such compositions. An aggregation inhibiting salt is included within these compositions to prevent aggregate and/or sediment formation upon the addition of $Fe^{+3}$ to the composition.

23 Claims, 3 Drawing Sheets

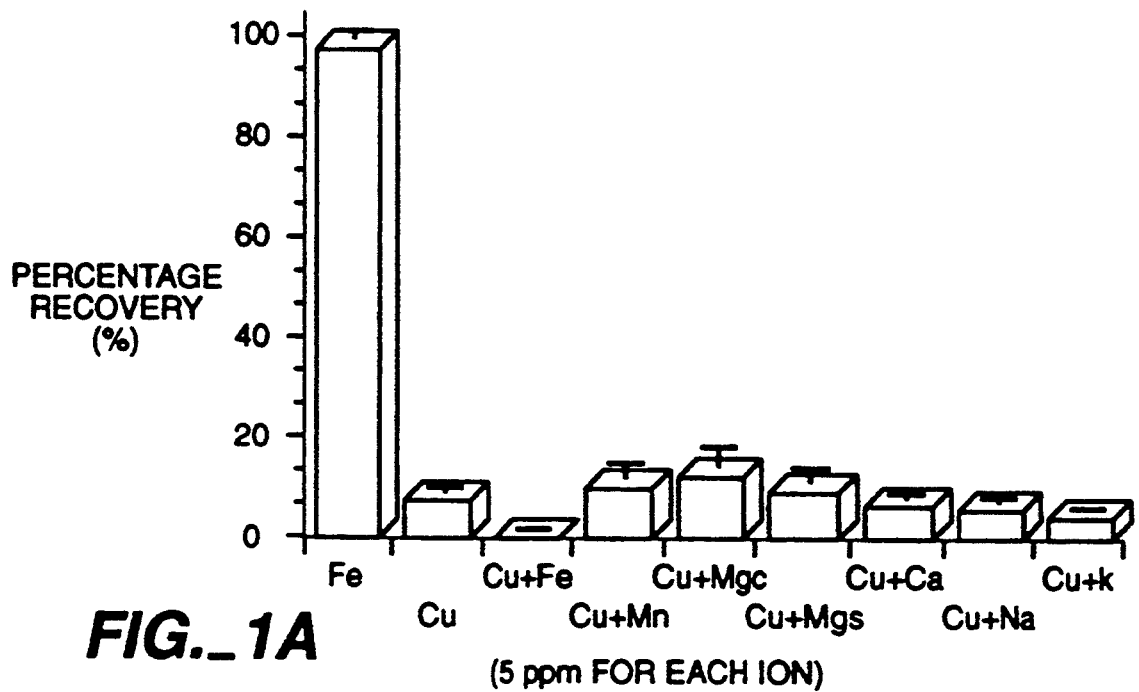
FIG._1A
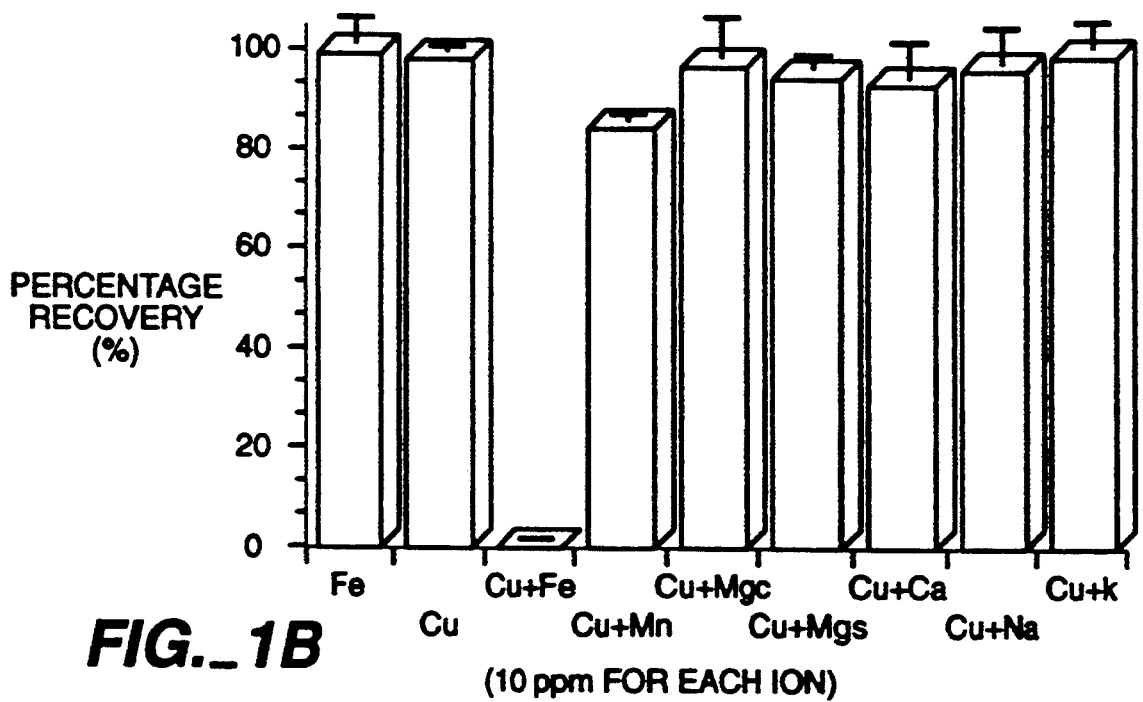
FIG._1B

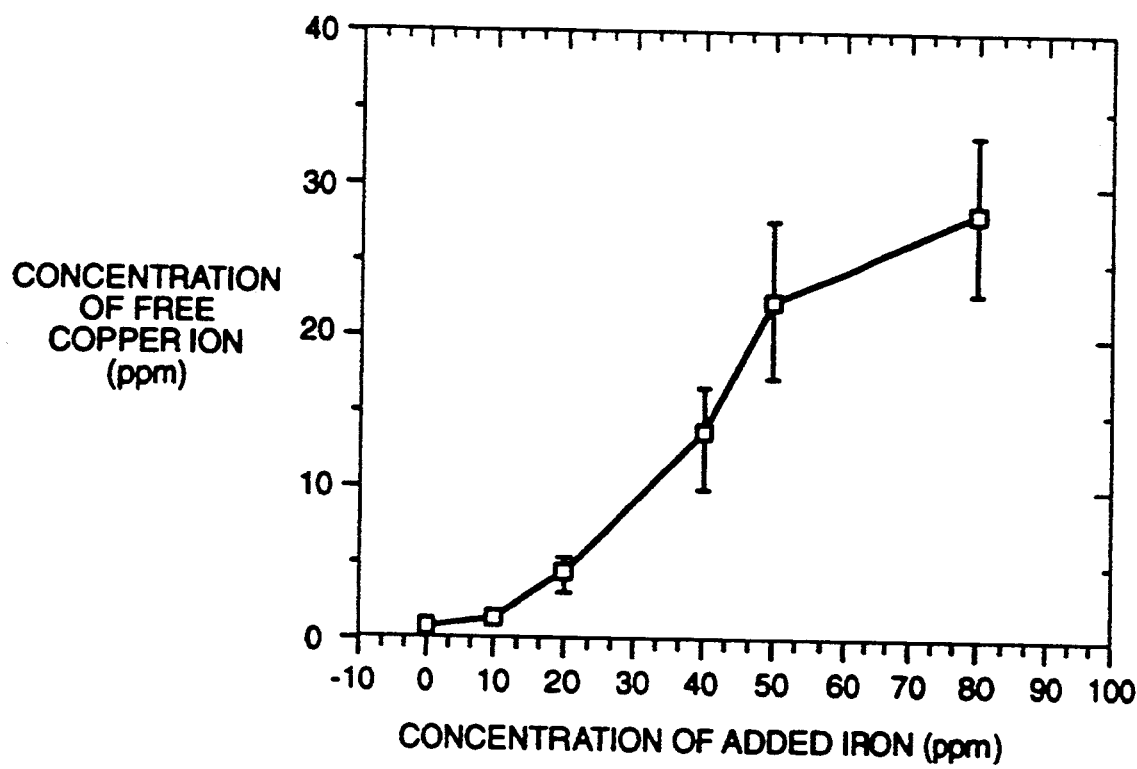
FIG._2
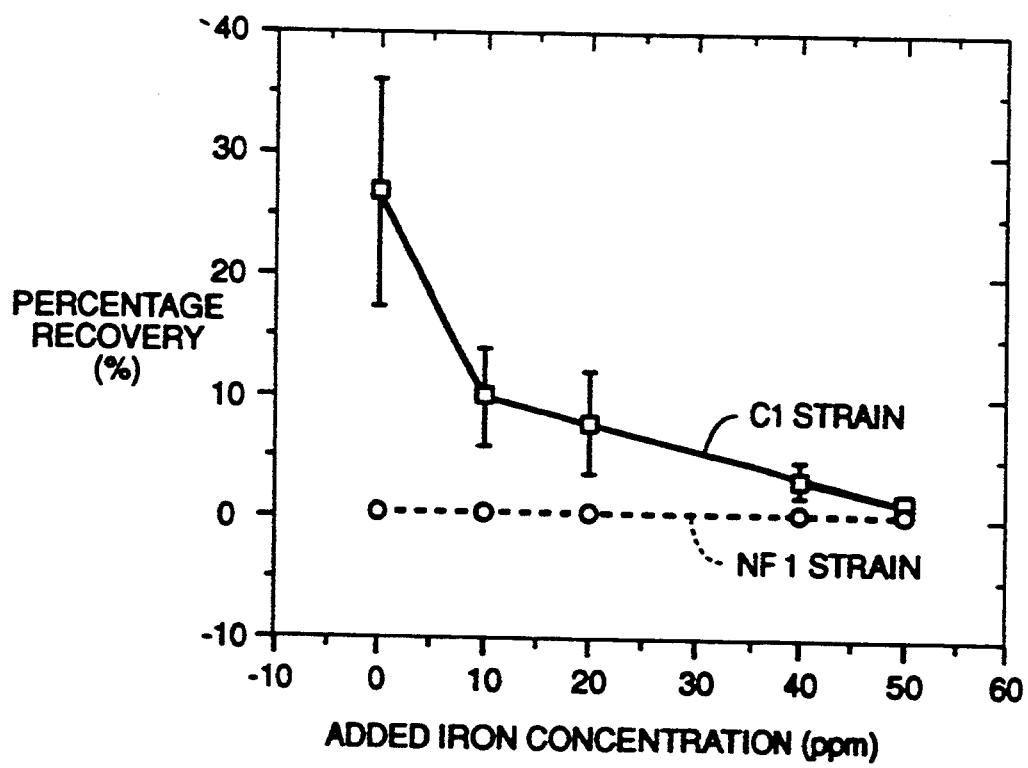
FIG._4

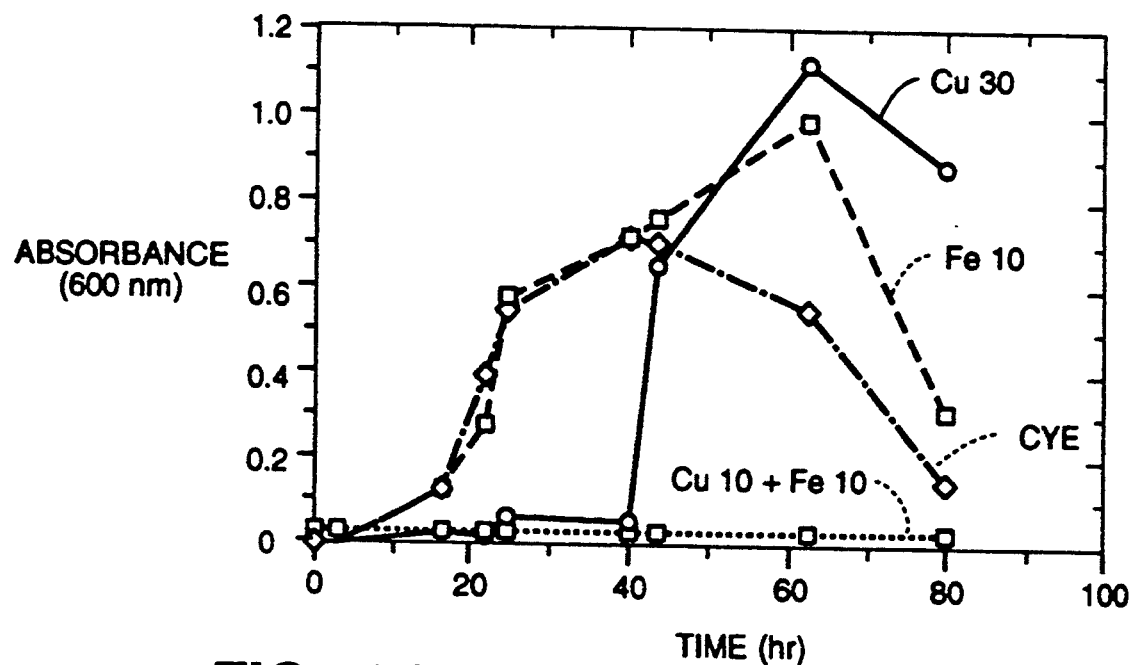
FIG._3A
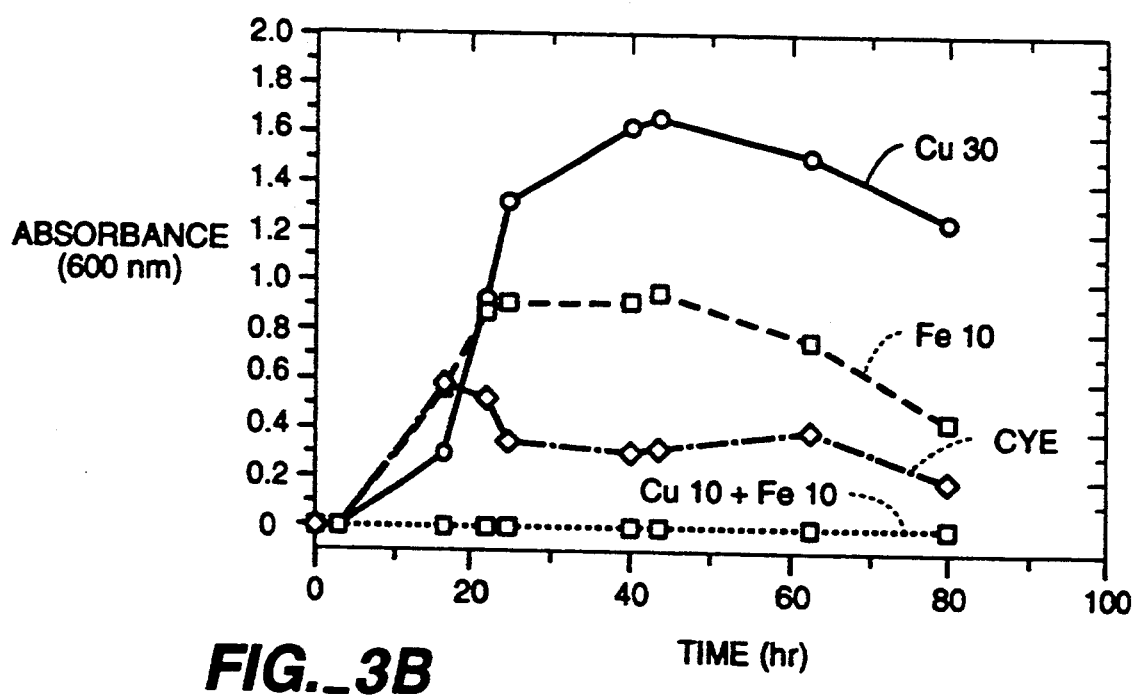
FIG._3B

METHODS FOR PREVENTING PRECIPITATION OF COPPER FROM COPPER BASED BACTERICIDAL COMPOSITIONS CONTAINING IRON

CROSS-REFERENCE TO RELATED APPLICATIONS

This application is a continuation-in-part of U.S. patent application Ser. No. 07/644,997 filed Jan. 22, 1991 (now U.S. Pat. No. 5,202,353), which application is incorporated herein by reference in its entirety.

BACKGROUND OF THE INVENTION

1. Field of the Invention

This invention is directed to methods for reducing aggregate and/or sediment formation in aqueous fixed copper based compositions containing $Fe^{+3}$ and to compositions produced by these methods.

2. State of the Art

The use of copper based compositions for agricultural uses is well known in the art. Such compositions are employed as bactericidal and/or fungicidal compositions and all of these compositions rely upon the toxic action of the free $Cu^{+2}$ ion (as opposed to chelated copper) which must penetrate into the microorganism in order to exert its toxic effect.

These copper based compositions are typically aqueous "fixed" copper based compositions because the copper compounds used in these compositions typically have a solubility of free $Cu^{+2}$ from about 1 to 30 ppm in the aqueous solution with the remainder (and the vast majority) of the copper either being insoluble or in chelated form (i.e., "fixed"). The 1 to 30 ppm of $Cu^{+2}$ in such aqueous compositions is typically referred to as "free copper" to distinguish it from either the chelated $Cu^{+2}$ or the insoluble $Cu^{+2}$ in these fixed copper compositions.

Because of their widespread use, some fungal and bacterial microorganisms have developed a dose dependent tolerance to aqueous fixed copper based fungicidal and/or bactericidal compositions. That is to say that such microorganisms are tolerant to fixed copper based fungicidal and/or bactericidal compositions at doses of free copper heretofore generally employed. At higher dosages, the increased amount of free copper in these compositions still exerts its toxic effect. However, the use of such higher dosages is not preferred for both economical and practical reasons.

As noted in allowed U.S. patent application Ser. No. 07/644,997 (U.S. Pat. No. 5,202,353), the use of up to about 300 ppm of $Fe^{+3}$ in fixed copper based fungicidal and bactericidal compositions synergistically enhances the toxic activity of the free $Cu^{+2}$ ions against fungi and bacteria. U.S. Patent application Ser. No. 07/644,997 is incorporated herein by reference in its entirety.

Notwithstanding the benefits of employing up to 300 ppm of $Fe^{+3}$ with fixed copper based fungicidal and bactericidal compositions, it has now been found that upon addition of $Fe^{+3}$ to fixed copper compositions, aggregates and/or sediment can form. Without being limited to any theory, it is believed that aggregation and sedimentation are related to the extent that formation of sufficiently large aggregates is a precursor of sediment formation and hence sediment formation is an extreme example of large aggregate formation.

In any event, aggregate and/or sediment formation is highly undesirable because they form larger particles whereas small particles are preferably delivered to the plant (the bacterial or fungal growth habitat) so as to obtain adequate coverage.

Accordingly, methods to inhibit formation of such aggregates and/or sediment and aqueous fixed copper based compositions containing $Fe^{+3}$ wherein aggregate and/or sediment formation is reduced would be highly desirable.

SUMMARY OF THE INVENTION

This invention is directed to the novel and unexpected discovery that the addition of certain salts to aqueous fixed copper based compositions reduces the size and rate of aggregate and/or sediment formation upon the addition of the $Fe^{+3}$.

Surprisingly, it has been found that the addition of these aggregate inhibiting salts must be prior to or simultaneous with the addition of the $Fe^{+3}$ to the aqueous fixed copper based compositions since the addition of such salts after the addition of the $Fe^{+3}$ does not result in any significant dissipation or reduction in size of the aggregates formed by the addition of the $Fe^{+3}$ to the fixed copper based composition and has very little effect on the sediment formed by such addition. Contrarily, the addition of these aggregate inhibiting salts to the aqueous fixed copper based composition prior to or simultaneous with the addition of the added $Fe^{+3}$ reduces the size and rate of aggregate and/or sediment formation upon the addition of the $Fe^{+3}$ to the fixed copper based composition.

Accordingly, in one of its method aspects, this invention is directed to a method for inhibiting aggregate and/or sediment formation upon the addition of $Fe^{+3}$ to an aqueous fixed copper based composition which method comprises the steps:

(a) selecting an aqueous fixed copper based composition which has a free $Cu^{+2}$ ion concentration of from 1 to 30 ppm;
 (b) adding an amount of an aggregate inhibiting salt to the composition so that upon the subsequent or simultaneous addition of up to 300 ppm of $Fe^{+3}$, the size and rate of aggregate and/or sediment formation in the composition is reduced; and
 (c) adding up to 300 ppm $Fe^{+3}$ to the composition.

In one embodiment, steps (b) and (c) are conducted sequentially. In another, steps (b) and (c) are conducted simultaneously by forming a first solution containing appropriate amounts of both the $Fe^{+3}$ and the aggregate inhibiting salt which is then added to an aqueous fixed copper based composition.

In one of its composition aspects, this invention is directed to an aqueous composition which comprises:

(a) water;
 (b) an effective amount of a fixed copper based compound so as to provide from 1 to 30 ppm of free $Cu^{+2}$ ions in solution;
 (c) an amount of an aggregate inhibiting salt so as to reduce the size and rate of aggregate and/or sediment formation resulting from the addition of up to 300 ppm of $Fe^{+3}$ to the composition; and
 (d) up to about 300 ppm of $Fe^{+3}$.

The aqueous compositions described above are suitable for controlling bacterial and/or fungal microorganisms. Accordingly, in another of its method aspects, the present invention is directed to a method for the control of bacteria which method comprises applying to said bacteria or their growth habitat a bactericidal composition which comprises:
(a) water;
(b) an effective amount of a fixed copper based bactericidal compound so as to provide from 1 to 30 ppm of free $Cu^{+2}$ ions in solution;
(c) an amount of an aggregate inhibiting salt so as to reduce the size and rate of aggregate and/or sediment formation of the $Cu^{+2}$ ions in the presence of the $Fe+3$; and
(d) up to about 300 ppm of $Fe^{+3}$.

In still another of its method aspects, the present invention is directed to a method for the control of fungi which method comprises applying to said fungi or their growth habitat a fungicidal composition which comprises:
(a) water;
(b) an effective amount of a fixed copper based fungicidal compound so as to provide from 1 to 30 ppm of free $Cu^{+2}$ ions in solution;
(c) an amount of an aggregate inhibiting salt so as to reduce the size and rate of aggregate and/or sediment formation of the $Cu^{+2}$ ions in the presence of the $Fe+3$; and
(d) up to about 300 ppm of $Fe^{+3}$.

BRIEF DESCRIPTION OF THE DRAWINGS

FIG. 1A illustrates the synergistic action of a copper based bactericidal compound and iron ($Fe^{+3}$) in killing copper-sensitive strains of walnut blight bacteria, *Xanthomonas campestris* pv. *juglandis*.

FIG. 1B illustrates the synergistic action of a copper based bactericidal compound and iron ($Fe^{+3}$) in killing copper-resistant strains of walnut blight bacteria, *Xanthomonas campestris* pv. *juglandis*.

FIG. 2 illustrates that spraying walnut leaves with a solution of Kocide 101 (a commercially available copper based bactericidal composition) amended with iron ($Fe^{+3}$) significantly increased the availability of free copper ions on the leaf surfaces as compared to the nonamended Kocide spray.

FIG. 3A and FIG. 3B show that the addition of iron ($Fe^{+3}$) increased the amount of free copper ions in the medium because of the decreased pH values, but also affected the physiology of the bacteria making them more sensitive to the toxic action of the copper ions. Data also show that copper resistant strains of *Xanthomonas campestris* pv. *juglandis* and *Pseudomonas syringae* pv. *syringae* grow well after a period of lag phase in the medium with 30 ppm added copper even though the medium had a low pH value and high free copper ion content (see Table 5). However, the bacteria did not grow well in a medium with 10 ppm each of copper and iron, which had a higher pH value and a lower content of free copper ions. This indicates that iron increased the susceptibility of the bacteria to the copper ions.

FIG. 4 illustrates that Kocide 101 reduced the population of a copper-sensitive strain of blight bacteria, but not a copper resistant strain. Kocide amended with iron ($Fe^{+3}$) significantly ($P=<0.05$) reduced leaf epiphytic populations of the copper-resistant blight strain compared to Kocide alone. The most effective treatment was Kocide amended with 50 ppm iron, which reduced populations of the bacteria to levels near zero.

DETAILED DISCLOSURE OF THE INVENTION

While copper based fungicidal and bactericidal compounds are important pesticides for controlling both fungi and bacteria, these compounds have suffered from the development of fungi and/or bacteria possessing a dose dependent tolerance to such compounds. Bacteria and fungi possessing such a dose dependent tolerance require higher doses of a fixed copper based compound to effect toxicity.

One method for countering this dose dependent tolerance of certain strains of bacteria and fungi is to add up to about 300 ppm of $Fe^{+3}$ to the aqueous fixed copper based fungicidal and/or bactericidal compositions. As noted in allowed U.S. patent application Ser. No. 07/644,997 (now U.S. Pat. No. 5,202,353), the use of this amount of $Fe^{+3}$ in combination with aqueous fixed copper compositions results in enhancement in the effectiveness of these compositions against fungi and bacteria, including fungi and bacteria possessing dose dependent tolerance to such fixed copper compositions.

Notwithstanding the above, it has now been found that the methods and compositions described in U.S. patent application Ser. No. 07/644,997 suffer from the drawback that the addition of up to about 300 ppm of $Fe^{+3}$ to aqueous fixed copper based compositions can result in aggregate and/or sediment formation in these compositions. Without being limited to any theory, it is believed that the aggregates and sediment so formed are complexes of free $Cu^{+2}$ and $Fe^{+3}$ ions. In any event, when aggregation and/or sedimentation occurs, it reduces the bactericidal and/or fungicidal effectiveness of the aqueous fixed copper based composition because it increases the size of particles applied to plants and other growth habitats for the bacteria and fungi which, in turn, diminishes the coverage of the fixed copper based composition onto such growth habitats.

This invention is directed to the unexpected and novel discovery that the addition of aggregate inhibiting salts to an aqueous fixed copper based fungicidal and/or bactericidal composition prior to or simultaneous with the addition of up to 300 ppm of $Fe^{+3}$ reduces the size and rate of aggregate and/or sediment formation upon the addition of $Fe^{+3}$ to this composition. The fact that such salts would reduce the size and rate of aggregate and/or sediment formation is particularly surprising.

However, prior to describing this invention in further detail, the following terms will first be defined.

The term "aqueous fixed copper based compositions" includes aqueous fixed copper based bactericidal and/or fungicidal compositions and refer to those aqueous compositions which possess toxicity to fungi and bacteria by virtue of having from about 1 to 30 ppm of free copper (unchelated and solubilized $Cu^{+2}$) in solution. The free copper penetrates into the bacterial and/or fungal microorganism in order to exert its toxic effect.

This amount of free copper in solution in such compositions is achieved by the use of fixed copper compounds which possess limited solubility in water. Such fixed copper compounds are well known in the art and the particular compound employed is not critical. Suitable fixed copper compounds include $Cu(OH)_2$, bordeaux, as well as other well known fixed copper compositions including those disclosed in CRC Handbook of Pest Management in Agriculture, Vol. 3, David Pimentel (Editor), CRC Press, Boca Raton, Fla. (1981), which is incorporated herein by reference.

There are a variety of commercially available fixed copper materials with tradenames such as KOCIDE (available from Griffin Ag Products, Valdosta, Ga.), COPPER COUNT-N (available from Mineral Research & Development Corp., Charlotte, N.C.) and CHAMPION (available from Agtrol Chemical Products, Houston, Tex.).

Preferably, the fixed copper compounds are formulated as a suspension in the aqueous composition and more preferably as an emulsifiable suspension.

In a preferred embodiment, the fixed copper compound employed in such aqueous compositions is one which slowly releases free copper into the environment so as to provide a concentration of free $Cu^{+2}$ ions of from about 1 ppm to about 30 ppm in the presence of up to about 300 ppm $Fe^{+3}$. The specific concentration of free $Cu^{+2}$ ions released by the aqueous fixed copper based composition depends, in part, upon the amount of $Fe^{+3}$ found in the composition.

Copper hydroxide is the preferred form of fixed copper that is used in most agricultural situations because it adheres to plant parts and further because there is a continuous release of the free copper ion.

The aqueous fixed copper based fungicidal and/or bactericidal compositions can include other compatible materials such as extenders, diluents, adjuvants, and the like. The fixed copper based compositions can be formulated and applied as emulsifiable concentrates, as suspensions, or as any of several other known types of formulations, depending on the desired mode of application. The formulation of emulsifiable concentrates and suspensions are well known in the art.

The term "$Fe^{+3}$" or "iron" refers to any water soluble form of $Fe^{+3}$ including ferric salts such as $FeCl_3$, $Fe_2(SO_4)_3$, ferric citrate, and the like. Also included within the term "$Fe^{+3}$" are ferrous ($Fe^{+2}$) salts which, when applied to the microorganism or its growth habitat, will in situ, form $Fe^{+3}$.

The specific water soluble iron ($Fe^{+3}$) compound employed in the present invention is not critical provided that it has a water solubility of at least 1 milligram per liter (i.e., is water soluble) and preferably at least 5 milligrams per liter. Without being limited to any theory, it is believed that it is the ferric ($Fe^{+3}$) ion which enhances the activity of the fixed copper based. fungicidal and/or bactericidal compounds and that the only criticality of the counter ion is that it imparts water solubility.

The amount of one or more iron ($Fe^{+3}$) compounds added to the aqueous fixed copper based fungicidal and/or bactericidal composition is an activity enhancing amount. That is to say that the amount of iron added to the composition is an amount sufficient to enhance the toxicity of the free copper to the fungi and/or bacteria. Preferably, iron ($Fe^{+3}$) concentrations effective in enhancing the activity of a copper based fungicidal and/or bactericidal compound are at least about 10 ppm of the fungicidal and/or bactericidal composition and more preferably from about 10 ppm to about 300 ppm and even more preferably from about 10 ppm to about 100 ppm.

It is noted that higher concentrations of $Fe^{+3}$ will cause increasing amounts of free $Cu^{+2}$ ions in solution and that such higher concentrations of $Fe^{+3}$ and/or free $Cu^{+2}$ ions can be phytotoxic to some plants. The specific concentration of free $Cu^{+2}$ and/or $Fe^{+3}$ required for phytotoxicity will vary depending on the plant, ambient conditions and other factors. However, in general, aqueous fixed copper based fungicidal and/or bactericidal compositions containing about 300 ppm or less of iron ($Fe^{+3}$) do not generate so much free copper so as to impart phytotoxicity to plants. Accordingly, the concentration of $Fe^{+3}$ employed in combination with the aqueous fixed copper based composition is preferably about 300 ppm or less. On the other hand, if phytotoxicity is not of any concern, then concentrations of iron ($Fe^{+3}$) of greater than 300 ppm can be used.

The term "aggregate inhibiting salts" refer to water soluble inorganic and organic salts which, when added to aqueous fixed copper based compositions in the absence of or simultaneously with added $Fe^{+3}$, will reduce the size and rate of aggregate and/or sediment formation when up to 300 ppm of $Fe^{+3}$ is either subsequently or simultaneously added to the composition.

In this regard, it is noted that salts which reduce the size and rate of aggregate formation also inhibit sediment formation. Specifically, without being limited to any theory, it is believed that aggregate and sediment formation are related to the extent that formation of sufficiently large aggregates is a precursor of sediment formation and hence sediment formation is an extreme example of large aggregate formation. Accordingly, it is further believed that salts which reduce the size and rate of aggregate formation will necessarily also reduce sediment formation. In any case, it is very important to reduce aggregate formation as it is highly desirable to have small particles of copper:iron complex delivered to plant parts which are infected with either a bacteria or fungus. Otherwise, coverage is not adequate and control of the bacterial and/or fungal infestations is reduced.

Water soluble aggregate inhibiting salts are those salts which are sufficiently water soluble so as to provide sufficient solubilized ions to reduce the size and rate of aggregate formation of the free $Cu^{+2}$ ions in the aqueous fixed copper based composition upon the addition of $Fe^{+3}$. Preferably, the aggregate inhibiting salts possess a water solubility, in the presence of the fixed copper composition of at least about 0.0001 g per ml and more preferably at least about 0.1 g per ml and even more preferably at least 1 gram per ml.

Suitable aggregate inhibiting salts are readily determined via a simple analytical test. Specifically, suitable aggregate inhibiting salts are determined by selecting a candidate aggregate inhibiting salt which is then added at the rate of 200 μg/ml to a KOCIDE composition (an aqueous fixed copper based suspension) containing 2.2 grams of copper hydroxide per liter of water and then 100 μg/ml of $Fe^{+3}$ as $FeCl_3 \cdot 6H_2O$ is added. The degree of sedimentation is then measured and is then compared to the control (i.e., the degree of sedimentation resulting from the addition of the same amount of $Fe^{+3}$ to the same KOCIDE composition in the absence of the candidate aggregate inhibiting salt). Since sedimentation is related to aggregation, candidate salts which reduce the degree of sedimentation upon addition of $Fe^{+3}$ by at least 10% compared to the control are deemed suitable aggregate inhibiting salts. Preferably, aggregation inhibiting salts reduce the degree of sedimentation in this test by at least 50% and more preferably by at least 75% as compared to control.

Preferred aggregate inhibiting salts include sulfate salts such as $M_{2/n}^{+n}SO_4^{-2}$ where M is an inorganic or organic cation having a positive charge of +n, salts of ethylene diamine tetraacetic acid (EDTA), and the like. Suitable organic cations include those having from 1 to 12 carbon atoms including pyridium, alkylammonium, dialkylammonium, trialkylammonium, tetraalkylammonium cations and the like. Suitable inorganic cations include those metals of Group Ia, Group IIa, Group VIIa, Group VIII (excluding iron), Group Ib, and Group IIb as defined by the periodic table set forth in Cotton & Wilkinson, "ADVANCED INORGANIC CHEMISTRY—A Comprehensive Text" Third Edition, Interscience Publishers (1972), as well as aluminum. Particularly preferred sulfate salts include $Mg^{+2}SO_4^{-2}$, $Mn^{+2}SO_4^{-2}$, $Zn^{+2}SO_4^{-2}$, $(NH_4^{+1})_2SO_4^{-2}$, $(K^{+1})_2SO_4^{-2}$, $(Al^{+3})_2(SO_4^{-2})_3$, and the like. Another preferred salt is a salt of ethylene diamine tetraacetic acid having up to 4 counterions of the formula $M^{+n}$.

Methodology

The practice of the invention is very simple and involves only the addition of an aggregate inhibiting salt to an aqueous fixed copper composition containing no added $Fe^{+3}$ in an amount effective in reducing the size and rate of aggregate and/or sediment formation in the composition upon the subsequent addition of up to 300 ppm $Fe^{+3}$.

Preferably, the aggregate inhibiting salt is added at a concentration of from about 5 to about 80 weight percent, and more preferably from about 35 to about 50 weight percent, based on the weight of the amount of fixed copper compound employed in this composition. The temperature of addition is not critical and addition is typically conducted under ambient conditions. The resulting composition is then mixed until the aggregate inhibiting salt is dissolved and, if necessary or desirable, the solution can be gently heated during mixing to facilitate dissolution.

The requisite amount of $Fe^{+3}$ is either added simultaneously with or after the addition of the aggregate inhibiting salt so as to provide, after mixing, an aqueous fixed copper based composition which can then be applied to bacteria and/or fungi or their growth habitat via conventional methods (i.e., spraying, etc.).

In regard to the above, it is noted that the addition of the aggregate inhibiting salt must be conducted prior to or simultaneously with the addition of added $Fe^{+3}$. Specifically, if the $Fe^{+3}$ is added prior to the aggregate inhibiting salt, this addition results in aggregate and/or sediment formation and the subsequent addition of the aggregate inhibiting salt is ineffective in significantly reducing the size of such preformed aggregates and/or removing the preformed sediment.

The invention will be further illustrated by the following examples, which are intended to be purely exemplary of the invention. In these examples, the following abbreviations have the following meanings:

CYE—casitone-yeast extract
gal.—gallon
lbs—pounds
mV—millivolts
nm—nanometers
ppm—parts per million
rpm—rotations per minute Examples 1–10 are presented to illustrate the synergy achieved by employing up to 300 ppm of $Fe^{+3}$ in combination with an aqueous fixed copper based composition in killing bacteria. Examples 11 and 12 are presented to illustrate the use of an aggregate inhibiting salt in such compositions.

EXAMPLES

Example 1

This example examines the effect on toxicity to the both a copper-sensitive bacterium (*Xanthomonas campestris* pv. *juglandis* strain NF) and a copper-resistant bacterium (*Xanthomonas campestris* pv. *juglandis* strain C 1) arising from combining different metal ions with free $Cu^{+2}$ ions. In particular, a known density of the bacteria were spread on different CYE-glycerol agar medium containing different kinds of metal ions. The metals employed were $Fe^{+3}$ (from $FeCl_3$ and reported as Fe); $Cu^{+2}$ (from $CuSO_4$ and reported as Cu); $Mn^{+2}$ (from $MnSO_4$ and reported as Mn); $Mg^{+2}$ (from $MgCl_2$ and reported as Mgc); $Mg^{+2}$ ($MgSO_4$ and reported as Mgs); $Ca^{+2}$ (from $CaCl_2$ and reported as Ca); $Na^{+}$(from NaCl and reported as Na); and $K^{+}$(from KCl and reported as K).

The recovery of cells or the number of colonies that grew were compared to the control (CYE-glycerol agar medium without metal amendments) which provides an estimate of the toxicity of the ions. The less cells that are recovered means that the kill of bacteria is better.

The results of these tests are shown in FIG. 1A (for the copper-sensitive bacterium) and in FIG. 1B (for the copper-resistant bacterium). In these figures, the results are given as a percentage recovery of the bacterium as compared to that recovered from the control. In particular, FIG. 1A illustrates that for the copper-sensitive bacterium, 5 ppm of an iron ($Fe^{+3}$) compound had little or no toxic effect whereas the addition of 5 ppm of copper resulted in a significant toxic effect regardless of whether the copper was used alone or in combination with other metal ions. In any event, the most toxic effect was seen for the copper/iron combination which resulted in substantially complete kill of all cells of the bacterium.

On the other hand, FIG. 1B illustrates that for the copper-resistant bacterium, the addition of 10 ppm of either an iron ($Fe^{+3}$) compound or a copper ($Cu^{+2}$) compound had little or no toxic effect on the bacterium. Likewise, FIG. 1B further illustrates that the addition of all combinations of 10 ppm of a copper ($Cu^{+2}$) compound with 10 ppm of other metal ions, except ferric ions, also had little or no toxic effect on the bacterium. However, the combination of 10 ppm of a copper ($Cu^{+2}$) compound with 10 ppm of an iron ($Fe^{+3}$) compound resulted in a substantially complete kill of all cells of the bacterium.

Accordingly, the results of these examples demonstrate that combinations of an iron ($Fe^{+3}$) compound and a free copper ($Cu^{+2}$) compound unexpectedly result in enhanced toxicity to bacteria and that these results are not shared by combinations of other metals with free copper.

Example 2

This example illustrates how varying concentrations of iron affect the synergistic action of iron and copper in killing copper sensitive or resistant bacteria. Specifically, copper resistant bacteria (*Xanthomonas campestris* pv. *vesicatoria* strain 81-23; *Pseudomonas syringae* pv. *syringae* strain A1513, and *Xanthomonas. campestris* pv. *juglandis*) were grown in the manner of Example 1 above at varying concentrations of copper and iron so as to determine concentrations of each required to inhibit the growth of these bacteria. The results of this example are reported in Tables 1–3 below. Table 1 describes the growth results for *Xanthomonas campestris* pv. *vesicatoria* copper-resistant strain 81-23 on the CYE-glycerol agar medium containing different concentrations of copper and iron.

TABLE 1

| added conc. of $Fe^{3+}$ (ppm) | Growth of X. c. pv. *vesicatorial*[1] added conc. of $Cu^{2+}$ (ppm) 40 | 30 | 20 | 10 | 0 |
|---|---|---|---|---|---|
| 0 | − | ± | + | + | + |
| 2.5 | − | ± | + | + | + |
| 5.0 | − | − | ± | + | + |
| 10.0 | − | − | − | + | + |

[1]The bacterium was streaked to the agar plates and grown at 28° C. for 2–3 days. + growth; ± poor growth; − no growth.

Table 2 describes the growth results for *pseudomonas syringae* pv. *syringae* copper-resistant strain A1513 on the CYE-glycerol agar medium containing different concentrations of copper and iron.

TABLE 2

| added conc. of $Fe^{3+}$ (ppm) | Growth of P. s. pv. *syringae*[2] added conc. of $Cu^{2+}$ (ppm) 40 | 30 | 20 | 10 | 0 |
|---|---|---|---|---|---|
| 0 | + | + | + | + | + |
| 2.5 | − | ± | + | + | + |
| 5.0 | − | − | ± | + | + |
| 10.0 | − | − | − | + | + |

[2]The bacterium was streaked to the agar plates and grown at 28° C. for 2–3 days. + growth; ± poor growth; − no growth.

Table 3 describes the growth results of *Xanthomonas campestris* pv. *juglandis* copper-resistant strain C1 on the CYE-glycerol agar medium containing different concentrations of copper and iron.

TABLE 3

| added conc. of $Fe^{3+}$ (ppm) | Growth of X. c. pv. *juglandis*[3] added conc. of $Cu^{2+}$ (ppm) 40 | 30 | 20 | 10 | 0 |
|---|---|---|---|---|---|
| 0 | ± | + | + | + | + |
| 2.5 | − | ± | + | + | + |
| 5.0 | − | − | ± | + | + |
| 10.0 | − | − | − | + | + |

[3]The bacterium was streaked to the agar plates and grown at 28° C. for 2–3 days. + growth; ± poor growth; − no growth The above data demonstrates that with increased concentrations of iron, less copper is needed to inhibit the growth of *Xanthomonas campestris* pv. *vesicatoria, Pseudomonas syringae* pv. *syringae,* and *Xanthomonas campestris* pv. *juglandis.*

Example 3

This example demonstrates that the addition of $Fe^{3+}$-(up to 200 ppm) to an aqueous copper based bactericidal composition (Kocide 101—available from Griffin Ag Products, Valdosta, Ga.) does not impede the ability of the cupric electrode to measure free copper ion ($Cu^{+2}$) concentrations. Specifically, the aqueous copper based bactericidal compositions were amended with $FeCl_3$(-where necessary) and then were centrifuged at 14,000 rpm for 30 minutes and the dissolved copper concentrations of supernatants were measured with an inductively coupled plasma (ICP) 40 emission spectrometer (Perkin-Elmer Corporation). On the other hand, free copper concentrations of Kocide solutions amended with $FeCl_3$(where necessary) were measured directly with a cupric specific electrode (Orion model 9429). The pH of the solution was measured with a pH meter. The results of this test are set forth in Table 4 below:

TABLE 4

| Added $Fe^{3+}$ (ppm) | Kocide Dissolved copper[4] (ppm) | Free copper[5] (ppm) | pH |
|---|---|---|---|
| 0.0 | 0.08 | 0.02 | 7.8 |
| 20.0 | 22.60 | 20.99 | 6.0 |
| 50.0 | 68.50 | 66.99 | 5.9 |
| 100.0 | 145.30 | 152.41 | 5.6 |
| 200.0 | 287.50 | 321.47 | 5.4 |

[4]Kocide solutions amended with $FeCl_3$ were centrifuged at 14,000 rpm for 30 min, and the dissolved copper concentrations of supernatants were measured with the inductively coupled plasma (ICP) 40 emission spectrometer (Perkin-Elmer corporation).
[5]Free copper concentrations of Kocide solutions amended with $FeCl_3$ were measured directly with a cupric specific electrode (Orion model 9429)

Example 5

Example 5 demonstrates that the addition of a soluble iron ($Fe^{3+}$) compound to the CYE glycerol broth medium decreased pH values and increased the availability of free copper ions. Specifically, the pH values and copper electrode potential (mV) were determined for CYE-glycerol broth containing different concentrations of added free copper ($Cu^{+2}$) and added iron ($Fe^{3+}$). The copper electrode potential (mV) was measured with a cupric specific electrode (Orion model 9429) and is proportional to logarithmic concentration of soluble free copper ion, i.e., 113 mV, 0.1 ppm; 146 mV, 1.0 ppm; 175 mV, 10.0 ppm. The results of this example are set forth in Table 5 below:

TABLE 5

| $Fe^{3+}$ | Added Conc. of $Cu^{2+}$ (ppm)[6] 5 | | 10 | | 20 | | 30 | | 40 | |
|---|---|---|---|---|---|---|---|---|---|---|
| Iron (ppm) | pH | mV | pH | mV | pH | mV | pH | mV | pH | mV |
| 0 | 6.78 | 12.4 | 6.51 | 52.2 | 5.78 | 104.4 | 5.42 | 133.3 | 5.12 | 150.4 |
| 1 | 6.73 | 16.3 | 6.39 | 56.8 | 5.80 | 106.8 | 5.38 | 134.6 | 5.08 | 151.2 |
| 5 | 6.46 | 28.6 | 6.10 | 76.3 | 5.50 | 120.7 | 5.21 | 140.8 | 5.00 | 155.1 |
| 10 | 5.88 | 61.5 | 5.65 | 101.2 | 5.19 | 133.4 | 4.98 | 147.8 | 4.82 | 159.9 |

[6]Each value given is a mean of six subsamples; the experiment was repeated once.

Example 6

As shown in Example 5 above, the addition of an iron ($Fe^{+3}$) compound to a laboratory growth medium containing a copper based bactericidal composition resulted in more free copper ($Cu^{+2}$) in the medium. This example demonstrates that the increased amount of free copper ($Cu^{+2}$) arising from the addition of an iron ($Fe^{+3}$) compound to the growth medium also arises when this combination is sprayed onto typical sites for application of such bacterial compositions, i.e., a walnut leaf surface.

In particular, concentrations of free copper ($Cu^{+2}$) were determined on walnut leaf surfaces sprayed with a Kocide 101 (a commercially available copper based bactericidal composition) solution at a concentration of 2 lb/100 gallons amended with different concentrations of the same iron ($Fe^{+3}$) compound. In each case, the amount of spray solution applied per unit area was kept constant and each experiment was repeated 3 times and each replication had three subsamples.

After spraying, the free copper concentration was determined by washing the leaf surface with water and determining the free copper concentration by measuring the copper electrode potential (mV) of the resulting aqueous solution with a cupric specific electrode (Orion model 9429).

The results of this example are set forth in FIG. 2 and each value is a mean of nine subsamples and is expressed as the mean ± the standard deviation (Std. Dev.). In particular, FIG. 2 illustrates that spraying walnut leaves with a solution of Kocide 101 amended with an iron ($Fe^{+3}$) compound significantly increased the amount of free copper on the leaf surfaces as compared to the nonamended Kocide spray.

Example 7

The above examples have demonstrated that the addition of iron ($Fe^{+3}$) increases the amount of free copper ($Cu^{+2}$) in the medium because of the decreased pH values. This example demonstrates that the enhanced toxic effect resulting from the addition of an iron ($Fe^{+3}$) compound to the free copper ($Cu^{+2}$) does not arise solely from increased amounts of free copper ($Cu^{+2}$) in the medium.

Specifically, this example analyzes the toxic effect of different concentrations of $Fe^{+3}$ metal ions with free $Cu^{+2}$ ions on the growth of copper-resistant bacteria (*Xanthomonas campestris* pv. *juglandis* strain 3E and *Pseudomonas syringae* pv. *syringae* copper-resistant strain A1513). This example was conducted by spreading a known concentration of these bacteria on different CYE-glycerol agar media containing different concentrations of $Fe^{+3}$ metal ions with free $Cu^{+2}$ ions. The concentration of metals employed were a control, i.e., 0 ppm $Fe^{+3}$ and 0 ppm $Cu^{+2}$ (reported in FIGS. 3A and 3B as CYE); an iron compound only, i.e., 10 ppm $Fe^{+3}$ and 0 ppm $Cu^{+2}$ (reported in FIGS. 3A and 3B as Fe 10); a copper compound only, i.e., 30 ppm of free $Cu^{+2}$ (reported in FIGS. 3A and 3B as Cu 30); and both an iron compound and a copper compound, i.e., 10 ppm of $Fe^{+3}$ and 10 ppm of $Cu^{+3}$ (reported as Cu10 +Fe$_{10}$ in FIGS. 3A and 3B).

The ability to inhibit growth of bacteria using these growth media was determined by measuring the absorbance of the growth media at 600 nm at various times. Specifically, the absorbance of the media correlates to growth occurring in the media with higher absorbance values indicating more growth. The results of this example are set forth in FIG. 3A, FIG. 3B and Table 5. Both of these figures establish that the combination of the free copper ($Cu^{+2}$) compound with an iron ($Fe^{+3}$) compound provides synergistic control over growth of the bacteria.

The data also show that both copper resistant bacterial strains grow well after a period of lag phase in the medium with 30 ppm added copper even though the medium had a low pH value and high free copper ion content (see Table 5). However, the bacteria did not grow in a medium with 10 ppm each of $Cu^{+2}$ and $Fe^{+3}$, which had a higher pH value and a lower content of free copper ($Cu+2$). This indicates that the enhanced activity of free copper ($Cu^{+2}$) in the presence of an iron ($Fe^{+3}$) compound does not arise solely because this combination lowers the pH of the medium, thereby resulting in increased concentrations of free copper ($Cu^{+2}$). In fact, these data demonstrate that the iron ($Fe^{+3}$) compound increases the susceptibility of the bacteria to free copper.

Example 8

This example compares the effect on toxicity to both a copper-sensitive bacterium (*Xanthomonas campestris* pv. *juglandis* strain NF 1) and a copper-resistant bacterium (*Xanthomonas campestris* pv. *juglandis* strain C 1) arising from treating walnut leaves infested with one of these microorganisms with compositions containing free copper ($Cu^{+2}$) plus specified amounts of an iron ($Fe^{+3}$) compound or with a composition containing free copper ($Cu^{+2}$) in the absence of an iron ($Fe^{+3}$) compound.

In particular, a known density of the bacteria was spread on individual walnut leaf surfaces which were then treated with Kocide 101 (2 lbs/100 gal) amended with different concentrations the same iron ($Fe^{+3}$) compound. In each case, the amount of spray solution applied per unit area was kept constant and each experiment was repeat 3 times and each replication had three subsamples.

The recovery of cells or the number of colonies that grew after treatment was compared to the control (leaves containing the bacterium but which were not treated with either a free copper composition or a free copper composition containing an iron compound). The results provide an estimate of the toxicity of the different combinations. The less cells that are recovered means that the kill of bacteria is better.

The results of this example are illustrated in FIG. 4 which provides the results as a mean of nine subsamples and the values reported in this figure are the mean of these subsamples and are expressed as the mean ± Std. Dev. In particular, FIG. 4 demonstrates that the copper sensitive strain was effectively killed by the addition of only free copper ($Cu^{+2}$) and that the addition of an iron ($Fe^{+3}$) compound has no additional effect because the amount of free copper is already sufficient to be toxic to this bacterium. On the other hand, this example further demonstrates that the copper-resistant bacterium was not completely killed by the amount of free copper employed but with increasing amounts of an iron ($Fe^{+3}$) compound, an enhancement in toxicity was seen.

Accordingly, the enhancement in toxicity achieved by the addition of an iron ($Fe^{+3}$) compound to a copper based bactericidal composition is seen not only in the CYE growth medium but also on suitable sites for application of this composition.

Example 9

This example investigates the effectiveness of a composition of this invention against walnut blight. Walnut blight arises by colonization of newly developing buds early in spring by bacteria, i.e., *Xanthomonas campestris* pv. *juglandis*. The bacteria then overwinter in these sites until the buds develop into shoots the following year. These symptomless buds harbor populations of blight bacteria of between 10,000 and 100,000 per bud. In general, colonization of buds does not occur until the first rains and the bacteria are generally first found on the external surfaces and then later within the buds.

This example examines the toxic effect achieved by spraying walnut buds with a free copper based bactericidal composition (2 lbs./100 gal of Kocide 101); with the same composition amended to contain 50 ppm of an iron ($Fe^{+3}$) compound; with a composition containing 50 ppm of an iron ($Fe^{+3}$) compound and no free copper; and with a control composition, i.e., no free copper and no iron ($Fe^{+3}$) compound.

New buds are formed in April and infestations occur during rainfall. Buds are the principal source of inoculum. Accordingly, spraying was initiated on April 16 and buds were sprayed 4 times at intervals of 7 to 10 days. First samples were collected on May 21 and second samples on June 3 after 3 inches of rain. The results of this example are set forth in Table 6 below:

TABLE 6

Percentage of walnut buds infested with *Xanthomonas campestris* pv. *juglandis* on walnut trees with different treatments.[7,8,9]

| Treatments | before rain | after rain |
|---|---|---|
| Kocide 101 | $10.7^{ab}$ | $23.3^a$ |
| Kocide 101 +50 ppm $Fe^{3+}$ | $3.3^a$ | $6.0^b$ |
| 50 ppm $Fe^{3+}$ | $17.9^{bc}$ | $68.7^c$ |
| Control | $28.3^c$ | $75.3^c$ |

[7] Values are the mean number for each treatment replicated five times in completely randomized design at two different experimental sites. 175–200 buds for each treatment were assayed for the presence of X. c. pv juglandis.
[8] Means with a column followed by the same letter are not significantly different (p = 0.05), least significant difference = 13.8 (before rain) and 16.1 (after rain).
[9] Kocide 101 was applied at the rate of 2 lb/100 gal. All treatments were applied to the Ashley variety of walnut.

The above results demonstrate that, after rainfall, the buds treated with the composition of this invention provided substantially better protection against walnut blight as compared to the buds treated with only Kocide 101 and that treatment with only iron ($Fe^{+3}$) was substantially equivalent to control. That is to say that treatment with an iron ($Fe^{+3}$) compound in the absence of a free copper compound provided little, if any, protection against the blight.

Example 10

This example ascertains to what extent siderophores are involved in the mechanism by which iron ($Fe^{+3}$) enhances the toxicity of a free copper based fungicidal and/or bactericidal composition. In particular, siderophores are iron ($Fe^{+3}$) chelating compounds generated by a microorganism in response to iron deprivation. Siderophores are released from the microorganism whereupon they can complex with solubilized $Fe^{+3}$ compounds. These siderophore complexes can then be scavenged from these siderophore complexes through the use of specific membrane transport systems.

As noted above, it is only free copper (uncomplexed $Cu^{+2}$) that imparts toxicity to the microorganism. Moreover, siderophores which complex iron ($Fe+3$) may also complex free copper thereby rendering it inactive. In such a situation, it is possible that the addition of iron ($Fe+3$) to the free copper based fungicidal and/or bactericidal composition enhances the activity of the free copper by providing an alternative or preferred site for siderophore complexation.

This example determines whether such a siderophore mechanism is involved in the activity enhancing effect of iron ($Fe^{+3}$). Specifically, this example employs a siderophore deficient variant of *Pseudomonas syringae* pv. *syringae*(S−) and a variant capable of siderophore production of *Pseudomonas syringae* pv. *syringae*(S+).

In each case, a known density of the bacteria was spread on different CYE-glycerol agar medium in a petri dish containing the same concentration of a free copper compound and an iron ($Fe^{+3}$) compound. If siderophore production was involved in the mechanism by which the iron ($Fe^{+3}$) compound enhanced the activity of the free copper compound, then it would be expected that inhibition of the S+ strain would be greater than that of the S− strain. However, after about 48–72 hours, the inhibition of both strains was not different. That is to say that the degree of inhibition of the S+ strain was equivalent to the degree of inhibition of the S− strain. These results demonstrate that siderophores are not involved in the mechanism by which the iron ($Fe^{+3}$) compound enhances the activity of the free copper based fungicidal and/or bactericidal composition.

In addition to enhancing toxic effect of a free copper based bactericidal composition, iron ($Fe^{+3}$) compounds also enhance the toxic effect of a free copper based fungicidal composition. Such fungi include, for instance, fungi responsible for bean powdery mildew (*Erysiphe polygoni*), tomato late blight (*Phytophthora infestans*), grape downy mildew (*Mopara viticola*), rice blast (*Piricularia oryzae*), and the like.

Lastly, in treating certain blights, it is contemplated that, in addition to treatment with a composition of this invention, treatment of the situs with a microorganism benign to the situs but which is antagonistic to the blight may enhance control of the blight. For example, in the case of walnut blight caused by *Xanthomonas campestris* pv. *juglandis*, it has been found that some buds are heavily populated with a yeast strain which is naturally inhibitory to the blight and a number of buds contained only the yeast. Moreover, the yeast appears to be tolerant to copper. Accordingly, cotreatment of a walnut blight situs with both a composition of this invention as well as such a yeast strain which is benign to the situs but antagonistic to the blight may improve the effect of the treatment.

Example 11

This example illustrates methods for ascertaining whether candidate aggregate inhibiting salts are effective in reducing the size and rate of aggregate and sediment formation in an aqueous fixed copper composition upon the subsequent addition of $Fe^{+3}$. Specifically, in this example, different salts were added at the rate of 200 μg/ml to a KOCIDE composition (an aqueous fixed copper based suspension) containing 2.2 grams of copper hydroxide per liter of water and then 100 μg/ml of $Fe^{+3}$ (as $FeCl_3 \cdot 6H_2O$) was added. The resulting composition was stirred and sediment formation was then observed. In all cases, the results of visual observation were corroborated by examining the composition under a microscope.

These results were then compared to control which is taken as the degree of sedimentation resulting from the addition of the same amount of $Fe^{+3}$ to the same KOCIDE composition in the absence of the candidate aggregate inhibiting salt.

The results of this test are set forth in Table 7 below:

TABLE 7

| CANDIDATE AGGREGATE INHIBITING SALT | ABILITY TO INHIBIT SEDIMENT FORMATION |
|---|---|
| NaCl | − |
| $CaCl_2$ | − |
| $MgCl_2$ | − |
| $MgSO_4$ | +++ |
| $MnSO_4$ | ++ |

TABLE 7-continued

| CANDIDATE AGGREGATE INHIBITING SALT | ABILITY TO INHIBIT SEDIMENT FORMATION |
|---|---|
| $ZnSO_4$ | ++ |
| $Al_2(SO_4)_3$ | ++ |
| $(NH_4)_2SO_4$ | ++ |
| $K_2SO_4$ | ++ |
| $K_2HPO_4$ | + |
| $KH_2PO_4$ | + |
| $KH_2PO_4$ | + |
| $NH_4H_2PO_4$ | + |

In Table 7 above, the ability to inhibit sediment formation upon addition of $Fe^{+3}$ is measured as follows:
− = unable to reduce sediment formation upon addition of $Fe^{+3}$ by at least 10% compared to control
+ = able to reduce sediment formation upon addition of $Fe^{+3}$ by at least 10% compared to control
++ = able to reduce sediment formation upon addition of $Fe^{+3}$ by at least 30% compared to control
+++ = able to reduce sediment formation upon addition of $Fe^{+3}$ by at least 50% compared to control The results of this example illustrate that some of the candidate salts were, in fact, suitable aggregate inhibiting salts in that they were able to reduce sediment formation by at least 10% as compared to control.

Further to the above, addition of the aggregate inhibiting salt after the addition of $Fe^{+3}$ was ineffective for reducing the size and rate of aggregate formation whereas the simultaneous addition of the aggregate inhibiting salt with the $Fe^{+3}$ to fixed copper based compositions does reduce the size and rate of aggregate and/or sediment formation. For example, addition of an appropriate amount of an aggregate inhibiting salt to an aqueous solution of $Fe^{+3}$ coupled with the addition of this solution to the fixed copper based composition reduces aggregate and/or sediment formation. One particular example of this aspect was the use of a solution obtained by combining the 0.48 grams of $FeCl_3 \cdot 6H_2O$ and 0.678 grams of ethylene diamine tetraacetic acid tetrasodium salt which were combined into 100 ml of water and the entire amount of this solution was then added to 900 ml of an aqueous Kocide solution to provide for 1 liter of a solution containing on a pro rata basis 2 lbs copper hydroxide per 100 gallons. In this example, the size and rate of sediment formed upon addition of $Fe^{+3}$ to the fixed copper composition was this example was reduced by at more than 50% as compared to control.

Other salts of EDTA can also be employed and are represented by $M^{+n}$ above.

In still another embodiment, the simultaneous addition of the requisite components can be conducted from a solid composition comprising the fixed copper compound, the aggregation inhibiting salt and the $Fe^{+3}$ compound in the appropriate amounts so that upon dilution in water, the resulting solution has from 1 to 30 ppm free $Cu^{+2}$ ions, a sufficient amount of an aggregation inhibiting salt to reduce the size and rate of aggregate and sediment formation (preferably from 5 to 80 weight percent based on the weight of the fixed copper based compound) and from 10 to 300 ppm $Fe^{+3}$.

Example 12

The purpose of this example is to illustrate that the addition of an aggregate inhibiting salt does not significantly reduce the effectiveness of $CU_{+2}/Fe^{+3}$ ions in controlling bacteria. Specifically, bacterial suspensions of copper resistant strain C5 of *Xanthomonas campestris* pv. *juglandis* were diluted to $10^6$ to $10^3$ cfu/ml in 5 ml of CYE-glycerol broth amended with aqueous solutions containing $Cu_{+2}SO_4^{-2} \cdot 5H_2O$ and optionally $Fe^{+3}Cl_3 \cdot 6H_2O$ or $Fe^{+3}Cl_3 \cdot 6H_2O$ and $Mg^{+2}SO_4^{-2} \cdot 7H_2O$. The cultures were placed on a rotating wheel housed in an incubator at 28° C. for 2–3 days. Afterwards, the cultures were observed for turbidity which is indicative of bacterial growth. The lack of turbidity was taken as an indication that the copper composition amended to the culture was toxic to the bacteria and the presence of turbidity was taken as an indication that the copper composition amended to the culture was not toxic to the bacteria.

The results of this analysis are set forth in Table 8 below. In Table 8, the plus (+) sign is used to indicate bacterial growth whereas the minus (−) sign is used to indicate bacterial kill.

TABLE 8

| CONCENTRATION OF METAL IONS[a] | bacteria present in culture $10^6$ | $10^5$ | $10^4$ | $10^3$ | pH | mV[b] |
|---|---|---|---|---|---|---|
| Cu10 | + | + | + | + | 6.5 | 52 |
| Cu20 | + | + | + | − | 5.8 | 104 |
| Cu30 | + | − | − | − | 5.4 | 133 |
| Cu10 + Fe10 | − | − | − | − | 5.6 | 102 |
| Cu10 + Mg20 + Fe10 | − | − | − | − | 5.2 | 100 |

[a]Cu10 = means that 10 μg/ml of $CuSO_4.5H_2O$ are added to the broth
Cu20 = means that 20 μg/ml of $CuSO_4.5H_2O$ are added to the broth
Cu30 = means that 30 μg/ml of $CuSO_4.5H_2O$ are added to the broth
Cu10 + Fe10 = means that 10 μg/ml of $CuSO_4.5H_2O$ and 10 μg/ml of $FeCl_3.6H_2O$ are added to the broth
Cu10 + Mg20 + Fe10 = means that 10 μg/ml of $CuSO_4.5H_2O$, 20 μg/ml of $MgSO_4.7H_2O$ and 10 μg/ml of $FeCl_3.6H_2O$ are added to the broth
[b] = copper electrode potential (mV) was measured with a cupric specific electrode (Orion model 9429) and is proportional to the logarithmic concentration of soluble free copper ions, e.g., 113 mV = 0.1 μg/ml; 146 mV = 1.0 μg/ml; 175 mV = 10.0 μg/ml.

The results of this example illustrate that the addition of the aggregate inhibiting salt does not significantly effect the toxicity of the $Cu_{+2}/Fe^{+3}$ composition to copper resistant strain C5 of *Xanthomonas campestris* pv. *juglandis*.

What is claimed is:

1. A method for inhibiting aggregate and/or sediment formation upon the addition of $Fe^{+3}$ to an aqueous fixed copper based bactericidal composition which method comprises:

(a) adding an amount of an aggregate inhibiting salt to an aqueous fixed copper based bactericidal composition which has a free $Cu^{+2}$ ion concentration from 1 to 30 ppm so that upon the subsequent or simultaneous addition of up to 300 ppm of $Fe^{+3}$ to this composition, the size and rate of aggregate and/or sediment formation in the composition is inhibited; and (b) adding up to 300 ppm $Fe^{+3}$ to the composition produced in (a) above.

2. The method according to claim 1 wherein the aggregate inhibiting salt has a water solubility of at least 0.0001 g/ml.

3. The method according to claim 1 wherein the aggregate inhibiting salt is selected from the group consisting of $M^{+n}{}_{2/n}{}^{+n}SO_4^{-2}$ where M is an inorganic or organic cation having a positive charge of +n and salts of ethylene diamine tetraacetic acid (EDTA).

4. The method according to claim 1 wherein the aggregate inhibiting salt is selected from the group consisting of $Mg^{+2}SO_4^{-2}$, $Mn^{+2}SO_4^{-2}$, $Zn^{+2}SO_4^{-2}$, $(NH_4^{+1})_2SO_4^{-2}$, $(K^{+1})_2SO_4^{-2}$, and $(Al^{+3})_2(SO_4^{-2})_3$.

5. The method according to claim 4 wherein the aggregate inhibiting salt is $Mg^{+2}SO_4^{-2}$.

6. The method according to claim 5 wherein the amount of $Fe^{+3}$ added to the composition is from 10 to 300 ppm.

7. The method according to claim 6 wherein the $Fe^{+3}$ is obtained from $FeCl_3$ and hydrates thereof.

8. An aqueous bactericidal composition which comprises:

(a) water;

(b) a bactericidally effective amount of a fixed copper based compound so as to provide from 1 to 30 ppm of free $Cu^{+2}$ ions in solution;

(c) an amount of an aggregate inhibiting salt so as to reduce the size and rate of aggregate and/or sediment formation resulting from the addition of up to 300 ppm of $Fe^{+3}$ to the composition; and (d) up to about 300 ppm of $Fe^{+3}$.

9. The composition according to claim 8 wherein the aggregate inhibiting salt has a water solubility of at least 0.0001 g/ml.

10. The composition according to claim 8 wherein the aggregate inhibiting salt is selected from the group consisting of $M^{+n}{}_{2/n}{}^{+n}SO_4{}^{-2}$ where M is an inorganic or organic cation having a positive charge of +n and salts of ethylene diamine tetraacetic acid (EDTA).

11. The composition according to claim 8 wherein the aggregate inhibiting salt is selected from the group consisting of $Mg^{+2}SO_4{}^{-2}$, $Mn^{+2}SO_4{}^{-2}$, $Zn^{+2}SO_4{}^{-2}$, $(NH_4{}^{+1})_2SO_4{}^{-2}$, $(K^{+1})_2SO_4{}^{-2}$, and $(Al^{+3})_2(SO_4{}^{-2})_3$.

12. The composition according to claim 11 wherein the aggregate inhibiting salt is $Mg^{+2}SO_4{}^{-2}$.

13. The composition according to claim 12 wherein the amount of $Fe^{+3}$ added to the composition is from 10 to 300 ppm.

14. The composition according to claim 13 wherein the $Fe^{+3}$ is obtained from $FeCl_3$ and hydrates thereof.

15. A method for the control of bacteria which method comprises applying to said bacteria or their growth habitat a bactericidal composition which comprises:

(a) water;

(b) an effective amount of a fixed copper based bactericidal composition so as to provide from 1 to 30 ppm of free $Cu^{+2}$ ions in solution;

(c) an amount of an aggregate inhibiting salt so as to reduce the size and rate of aggregate and/or sediment formation of the $Cu^{+2}$ ions in the presence of the $Fe^{+3}$; and (d) up to about 300 ppm of $Fe^{+3}$.

16. The method according to claim 15 wherein the aggregate inhibiting salt has a water solubility of at least 0.0001 g/ml.

17. The method according to claim 15 wherein the aggregate inhibiting salt is selected from the group consisting of $M^{+n}{}_{2/n}{}^{+n}SO_4{}^{-2}$ where M is an inorganic or organic cation having a positive charge of +n and salts of ethylene diamine tetraacetic acid (EDTA).

18. The method according to claim 15 wherein the aggregate inhibiting salt is selected from the group consisting of $Mg^{+2}SO_4{}^{-2}$, $Mn^{+2}SO_4{}^{-2}$, $Zn^{+2}SO_4{}^{-2}$, $(NH_4{}^{+1})_2SO_4{}^{-2}$, $(K^{+1})_2SO_4{}^{-2}$, and $(Al^{+3})_2(SO_4{}^{-2})_3$.

19. The method according to claim 18 wherein the aggregate inhibiting salt is $Mg^{+2}SO_4{}^{-2}$.

20. The method according to claim 19 wherein the amount of $Fe^{+3}$ added to the composition is from 10 to 300 ppm.

21. The method according to claim 20 wherein the $Fe^{+3}$ is obtained from $FeCl_3$ and hydrates thereof.

22. A method for the control of fungi which method comprises applying to said fungi or their growth habitat a fungicidal composition which comprises:

(a) water;

(b) an effective amount of a fixed copper based fungicidal composition so as to provide from 1 to 30 ppm of free $Cu^{+2}$ ions in solution;

(c) an amount of an aggregate inhibiting salt so as to reduce aggregate and/or sediment formation of the $Cu^{+2}$ ions in the presence of the $Fe^{+3}$; and (d) up to about 300 ppm of $Fe^{+3}$.

23. The method according to claim 1 wherein the aggregate inhibiting salt is a salt of ethylene diamine tetraacetic acid.

* * * * *